United States Patent
Zihlmann et al.

(10) Patent No.: US 10,646,619 B2
(45) Date of Patent: May 12, 2020

(54) BONE SUBSTITUTE MATERIAL

(71) Applicant: GEISTLICH PHARMA AG, Wolhusen (CH)

(72) Inventors: Claudio Zihlmann, Lucerne (CH); Michael Bufler, Reinach (CH)

(73) Assignee: GEISTLICH PHARMA AG, Wolhusen (CH)

( * ) Notice: Subject to any disclaimer, the term of this patent is extended or adjusted under 35 U.S.C. 154(b) by 0 days.

(21) Appl. No.: 16/220,320

(22) Filed: Dec. 14, 2018

(65) Prior Publication Data
US 2019/0209737 A1 Jul. 11, 2019

(30) Foreign Application Priority Data
Dec. 14, 2017 (EP) .................................. 17207233

(51) Int. Cl.
| | |
|---|---|
| *A61L 27/12* | (2006.01) |
| *A61L 27/32* | (2006.01) |
| *A61K 33/42* | (2006.01) |
| *A61K 9/14* | (2006.01) |
| *A61K 9/16* | (2006.01) |
| *A61L 27/42* | (2006.01) |
| *A61L 27/58* | (2006.01) |
| *A61L 24/00* | (2006.01) |
| *A61L 27/36* | (2006.01) |
| *A61L 27/50* | (2006.01) |

(52) U.S. Cl.
CPC ............. *A61L 27/425* (2013.01); *A61L 27/12* (2013.01); *A61L 27/32* (2013.01); *A61L 27/58* (2013.01); *A61L 24/0063* (2013.01); *A61L 27/3608* (2013.01); *A61L 27/50* (2013.01); *A61L 2400/12* (2013.01); *A61L 2400/18* (2013.01); *A61L 2430/02* (2013.01)

(58) Field of Classification Search
CPC .... A61L 2430/02; A61L 27/12; A61L 27/425; A61L 27/32; A61K 6/54; A61K 9/14
See application file for complete search history.

(56) References Cited

U.S. PATENT DOCUMENTS

| | | | | |
|---|---|---|---|---|
| 5,958,504 A | * | 9/1999 | Lee .......................... | A61L 27/32 427/2.24 |
| 2012/0130506 A1 | * | 5/2012 | Bufler .................. | A61L 24/0063 623/23.61 |
| 2014/0127392 A1 | * | 5/2014 | Berckmans, III ...... | A61B 17/86 427/2.27 |
| 2015/0024023 A1 | * | 1/2015 | Gibson ................... | C01B 25/32 424/423 |
| 2016/0144071 A1 | * | 5/2016 | Bufler ..................... | A61L 27/24 424/426 |

FOREIGN PATENT DOCUMENTS

WO 2010/149296 A1 12/2010

OTHER PUBLICATIONS

Gittens et al. Implant Osseointegration and the Role of Microroughness and Nanostructures: Lessons for Spine Implants. Acta Biomater. Author manuscript. Aug. 1, 2015. (Year: 2015).*
Borum-Nicholas, L., et al: "Surface modification of hydroxyapatite. Part I. Dodecyl alcohol", Biomateri, Elsevier Science Publishers BV., Barking, GB, vol. 24, No. 21, (2003), pp. 3671-3679.
European Search Report cited in EP 17 20 7233, dated Jun. 14, 2018, 6 pages.

* cited by examiner

*Primary Examiner* — Tracy Liu
(74) *Attorney, Agent, or Firm* — Rothwell, Figg, Ernst & Manbeck, P.C.

(57) ABSTRACT

A biphasic calcium phosphate/hydroxyapatite (CAP/HAP) bone substitute material having a sintered CAP core and at least one closed epitactically grown layer of nanocrystalline HAP deposited on the external surface of the sintered CAP core, whereby the epitactically grown nanocrystals have the same size and morphology as human bone mineral, wherein the closed epitactically grown layer of nanocrystalline HAP deposited on the external surface of the sintered CAP core has a non-homogeneous external surface comprising individual clusters of flat crystal platelets consisting of epitactically grown HAP nanocrystals and coarse areas between the individual clusters, whereby the percentage of the coarse areas between the individual clusters as measured by SEM is at least 20% of the total surface, which material shows an increased capacity to induce bone formation, and a process of preparation thereof.

18 Claims, 3 Drawing Sheets

BONE SUBSTITUTE MATERIAL

CROSS-REFERENCE TO RELATED APPLICATIONS

The present application claims priority benefit of European Patent Application No. 17207233.2, filed on Dec. 14, 2017, the disclosure of which is incorporated herein by reference.

BACKGROUND

The invention relates to a new biphasic bone substitute material with a bilayer structure based on calcium phosphate/hydroxyapatite (CAP/HAP) which has a non-homogeneous external surface, a process for preparing that material and the use thereof as implant or prosthesis to support bone formation, bone regeneration, bone repair and/or bone replacement at a defect site in a human or animal.

Defects in bone structure arise in a variety of circumstances, such as trauma, disease, and surgery and there is still a need for effective repair of bone defects in various surgical fields.

Numerous natural and synthetic materials and compositions have been used to stimulate healing at the site of a bone defect. A well-known natural, osteoconductive bone substitute material that promotes bone growth in periodontal and maxillofacial osseous defects is Geistlich Bio-Oss® commercially available from Geistlich Pharma AG. That material is manufactured from natural bone by a process described in U.S. Pat. No. 5,167,961, which enables preservation of the trabecular architecture and nanocrystalline structure of the natural bone, resulting in an excellent osteoconductive matrix which is not or very slowly resorbed.

Tricalcium phosphate/hydroxyapatite (TCP/HAP) systems and their use as bone substitute materials are described, for example, in U.S. Pat. No. 6,338,752 disclosing a process for preparing a biphasic cement of α-TCP/HAP by heating a powder mixture of ammonium phosphate and HAP at 1200-1500° C.

European Patent EP-285826 describes a process for the production of a layer of HAP on metallic and non-metallic bodies for implants by application of a layer of α-TCP and completely converting the α-TCP layer into HAP by reaction with water of pH 2 to 7 at 80-100° C. The product obtained is a metallic or non-metallic body covered with a layer of HAP.

WO 97/41273 describes a process for coating a substrate such as notably hydroxyapatite (HAP) or other calcium phosphates (CAP) with a coating of carbonated hydroxyapatite, i.e. hydroxyapatite wherein phosphate and/or hydroxyl ions are partially replaced by bicarbonate ions, by a process comprising (a) immersing the substrate in a solution of pH 6.8 to 8.0 containing calcium ions, phosphate ions and bicarbonate ions at a temperature lower than 50° C., (b) heating the portion of the solution in contact with the substrate to a temperature of 50 to 80° C. until having a pH greater than 8, (c) maintaining the substrate in contact with the alkali solution obtained in step (b) to form a carbonated hydroxyapatite coating, and (d) taking the substrate off the solution and subjecting the coating to drying. The bicarbonate ions are disclosed to act as inhibitors of hydroxyapatite crystal growth, resulting in non-stoichiometric crystals containing defects and having rather small dimensions, namely 10-40 nm in length and 3-10 nm in width (see page 7, lines 1-7).

The components of calcium phosphate/hydroxyapatite (CAP/HAP) systems, especially TCP/HAP systems differ in their thermodynamic stability. Due to this difference, when CAP/HAP systems are implanted into a mammal, in particular a human patient, the solubility of TCP and other calcium phosphates is higher in the body fluid than the solubility of HAP. The difference in solubility between calcium phosphates and HAP causes a breakdown of the unordered sinterstructure of the CAP/HAP system because the better soluble compound CAP (e.g. TCP) is removed quicker than HAP. The sintered interconnection between CAP and HAP produced at high temperatures will also make a remarkable contribution to higher solubility of the device in the physiological environment. Two different types of reactions dominate accelerated in-vivo degradation of such ceramics: Chemical dissolution and biological resorption by cells. Both processes cause dissolution of the ceramic material, which furthermore causes a local oversaturation of calcium ions, whereby there are more calcium ions released than calcium ions adsorbed. The natural equilibrium of calcium ions no longer exists, neither in the extracellular matrix nor in the tissue surrounding of the implant. The local disturbance of the natural calcium equilibrium in terms of oversaturation of calcium ions leads to an increased osteoclast activity and therefore to an accelerated ill-controlled resorption of the ceramic material and a risk of adverse inflammation reactions, especially when using a large amount of synthetic bone substitute material.

When bone substitute material Geistlich Bio-Oss® is implanted into a human patient, the natural calcium equilibrium is practically not affected, the concentration of calcium ions on the surface of the material and within the local environment thereof remaining almost constant. Biological resorption of the material hence does not take place or proceeds at a very slow rate without the risk of adverse inflammation reactions.

EP-B1-2445543 discloses a highly advantageous calcium phosphate/hydroxyapatite (CAP/HAP) bone substitute material which, like bone substitute material Geistlich Bio-Oss®, after being set in vivo enables the concentration of calcium ions on the surface of the material and within the local environment thereof to remain almost constant and thus does not lead to an increased osteoclast activity.

Indeed, the natural calcium equilibrium which is necessary for optimal bone regeneration is not disturbed or destroyed. Moreover, the natural calcium concentration equilibrium is lastingly supported by the bone substitute material until the regeneration process is completed. When those conditions are met there is no increase of osteoclast activity, hence no risk of adverse inflammation reactions.

The invention of EP-B1-2445543 relates to a biphasic calcium phosphate/hydroxyapatite (CAP/HAP) bone substitute material comprising a sintered CAP core and at least one uniform and closed epitactically grown layer of nanocrystalline HAP deposited on top of the sintered CAP core, whereby the epitactically grown nanocrystals have the same size and morphology as human bone mineral, i.e. a length of 30 to 46 nm and a width of 14 to 22 nm.

The sintered CAP core may comprise tricalcium phosphate (TCP), notably α-TCP (α-Ca$_3$(PO$_4$)$_2$) or β-TCP (β-Ca$_3$(PO$_4$)$_2$), and/or tetracalcium phosphate (TTCP) Ca$_4$(PO$_4$)$_2$O.

According to a frequently used embodiment the sintered CAP core essentially consists of TCP, α-TCP being preferred.

The epitactically grown layer of nanocrystalline HAP is structurally and chemically nearly identical to the natural human bone mineral.

The epitactically grown layer of nanocrystalline HAP generally has a thickness of at least from 15 to 50 nm, preferably at least from 20 to 40 nm, more preferably at least from 25 to 35 nm. That minimum thickness corresponds to one layer of HAP nanocrystals in epitaxial orientation.

The epitactically grown layer of nanocrystalline HAP may comprise a single or multiple layers of HAP nanocrystals in epitaxial orientation. The thickness of the epitactically grown layer of nanocrystalline HAP, which is related to the number of such layers of HAP nanocrystals in epitaxial orientation, will be selected according to the intended application of the bone substitute material as implant or prosthesis in differently loaded parts of the body. The bone substitute material of that invention is indeed designed to function in vivo as a living-like system progressively transforming the sintered CAP core into hydroxyapatite similar in size and morphology to human bone mineral, the rate of that transformation being dependent on the rate of calcium release by the sintered CAP core, which is to a large extent controlled by the thickness of the epitactically grown layer of nanocrystalline HAP.

The properties of the CAP/HAP bone substitute material are to a large extent controlled by the thickness of the epitactically grown layer of crystalline HAP. The term "properties" includes the ability of the CAP/HAP bone substitute to release a constant concentration of calcium ions to the local environment in vitro and in vivo.

The thickness of the epitactically grown layer of nanocrystalline HAP is related to the ratio of the sintered CAP core material to HAP, said ratio being generally between 5:95 and 95:5, preferably from 10:90 to 90:10.

The CAP/HAP bone substitute material may be a particulate or a granulate, the particles or granules having a desired size and shape. Generally, the particles or granules are approximately spherical and have a diameter of 250 to 5000 µm.

The CAP/HAP bone substitute material may also be a shaped body, e.g. a screw, a nail, a pin or a structure having the profile of an osseous body part such as notably a hip, a clavicle, a rib, a mandible or a skull part. Such a screw, a nail or a pin may be used in reconstructive orthopedic surgery for fixing a ligament to a bone, for example in the knee or the elbow. Such a structure having the profile of an osseous body part may be used in orthopedic surgery as prosthesis for replacing a missing or defective bone or bone part.

That CAP/HAP bone substitute material of EP-B1-2445543 is taught to be obtained by a process comprising the steps of a) preparing a sintered CAP core material,
b) immersing the sintered CAP core material in an aqueous solution at a temperature between 10° C. and 50° C. to start the transformation process of CAP to HAP, whereby a uniform and closed epitactically grown layer of nanocrystalline hydroxyapatite is formed on the sintered CAP core material surface, the epitactically grown nanocrystals having the same size and morphology as human bone mineral,
c) stopping the transformation by separating the solid material from the aqueous solution at a time when a uniform and closed coating of at least one nanocrystalline layer of HAP is present but before the transformation process is finished completely,
d) optionally sterilizing the separated material coming from step c).

The preparation of the sintered CAP core material may be performed by methods known in the art comprising first mixing powders of calcium hydrogen phosphate ($CaHPO_4$), calcium carbonate and/or calcium hydroxide, then calcining and sintering the mixture within an appropriate temperature range, thereby giving a bulk sintered CAP core material (see e.g. Mathew M. et al., 1977, Acta. Cryst. B33: 1325; Dickens B. et al., 1974, J. Solid State Chemistry 10, 232; and Durucan C. et al., 2002, J. Mat. Sci., 37:963).

A bulk sintered TCP core material may thus be obtained by mixing powders of calcium hydrogen phosphate ($CaHPO_4$), calcium carbonate and/or calcium hydroxide in stoichiometric ratio, calcining and sintering the mixture at a temperature in the range of 1200–1450° C., preferably about 1400° C.

A bulk sintered TTCP core material may also be obtained by the above described process.

The bulk sintered CAP material prepared by such methods may be porous with a porosity of 2 to 80 vol % and a wide distribution of pores. The porosity parameters will be selected according to the intended application of the CAP/HAP bone substitute material.

The sintered CAP core material used in step b) may be
  the bulk sintered CAP core material prepared as described above,
  a particulate or granulate of sintered CAP core material obtained from the bulk sintered CAP core material prepared as described above, by using conventional methods such as crushing, grinding and/or milling, and sieving, or
  a preform of sintered CAP core material having a desired shape and size, e.g. a screw, a nail, a pin or a structure having the profile of an osseous body part.

Such a preform of any desired shape and size may be obtained from the bulk sintered core material prepared as described above, by using well known prototyping techniques such as CNC milling or 3D printing (see for example Bartolo P. et al., 2008, Bio-Materials and Prototyping Applications in Medicine, Springer Science New York, ISBN 978-0-387-47682-7; Landers R. et al., 2002, Biomaterials 23(23), 4437; Yeong W.-Y. et al., 2004, Trends in Biotechnology, 22 (12), 643; and Seitz H. et al., 2005, Biomed. Mater. Res. 74B (2), 782).

The aqueous solution of step b) is taught to be pure water, a simulated body fluid or a buffer. Important is that the pH value of the immersing solution of step b) is nearly neutral and remains stable throughout the transformation process, preferably within a pH range from 5.5 to 9.0.

The term "simulated body fluid" refers to any solution that mimics a body fluid. Preferably, the simulated body fluid has an ion concentration similar to that of blood plasma.

The buffer may be any buffer in the above pH range but is preferably a phosphate buffer with or without calcium, magnesium and/or sodium.

The buffer used in the Examples (see Examples 4 and 5) is an aqueous phosphate buffer.

The temperature range in step b) is generally between 10° C. and 50° C., preferably between 25 and 45° C., more preferably between 35° C. and 40° C.

The immersing step b) induces in a first phase a first-order phase transition of the CAP core material and therefore the nucleation of HAP nanocrystal precursors. During the second phase the resulting HAP precursors from the first phase will grow and establish a closed (i.e. completely coating) epitactic nanocrystalline composite layer. The first HAP nanocrystal layer must be uniform and closed and epitaxially connected to the sintered CAP core material.

During a third phase the first-order phase transition may proceed within the newly formed bilayer composite to further transform the sintered CAP core material (TCP or TTCP) into nanocrystalline HAP. During this third step of phase transition calcium ions will be released for a controllable time by a slow diffusion controlled process until a part of the sintered CAP core material has been transformed into nanocrystalline HAP. The thickness of the HAP layer and therefore the rate of calcium release can be controlled by variation of the transformation time.

The epitactically grown nanocrystalline HAP layer of appropriate thickness will be prepared in-vitro, the transformation of CAP into HAP being stopped before it is completed.

As soon as the CAP/HAP bone substitute material is set in vivo the transformation process of CAP into HAP will be reactivated by contact with the body fluids and the bone substitute material will function as a living-like system forming new hydroxyapatite similar in size and morphology to human bone mineral. During the in vivo phase transformation process the transported calcium ions will be released into the local environment supporting the local calcium equilibrium which is important and beneficial for bone regeneration processes.

Due to different regeneration times of bone defects in differently loaded regions of the body it is important that the rate of calcium release can be controlled. This can be achieved by variation of the thickness of the epitactically grown layer of hydroxyapatite.

Step c) is therefore a very critical step. The exposure time in the aqueous solution of step b) is based upon the thickness of the HAP layer desired. At least one layer of nanocrystalline HAP in epitaxial orientation is necessary. It is essential that the transformation of CAP into HAP is not finished.

The proper exposure time according to the thickness desired can be calculated by using several thermodynamic differential equations well known to the skilled person in the art of calcium phosphates, cement and concrete chemistry.

See for example: Pommersheim, J. C.; Clifton, J. R. (1979) Cem. Conc. Res.; 9:765; Pommersheim, J. C.; Clifton, J. R. (1982) Cem. Conc. Res.; 12:765; and Schlüssler, K. H. Mcedlov-Petrosjan, O. P.; (1990): Der Baustoff Beton, VEB Verlag Bauwesen, Berlin.

Transferring the solution of the above mentioned differential equations to the CAP/HAP system enables the prediction of the phase transition of CAP into HAP and the thickness of the layer such that the epitactic layer of HAP can be prepared in a stable and reproducible manner.

Separating the solid material from the aqueous solution at the end of step c) is usually performed by filtration, washing and drying, using techniques well known in the art.

In the Examples of EP-B1-2445543 (namely Example 4 [0057] and Example 5 [0058]), washing is performed by washing the separated granules of the bone substitute material 3 times with purified water to remove residuals from the buffered solution.

The optional sterilizing step d) may be performed by techniques well known in the art such as gamma-irradiation or X-ray radiation.

Using as taught in Examples 4 and 5 of EP-B1-2445543 an aqueous phosphate buffer for the aqueous solution of step b) and purified water to wash 3 times the separated granules at the end of step c), one obtains a biphasic calcium phosphate/hydroxyapatite (CAP/HAP) bone substitute material comprising a sintered CAP core and a uniform and closed epitactically grown layer of nanocrystalline HAP deposited on the external surface of the sintered CAP core, whereby the epitactically grown nanocrystals have the same size and morphology as human bone mineral, wherein the closed epitactically grown layer of nanocrystalline HAP deposited on the external surface of the sintered CAP core has a non-homogeneous external surface comprising individual (separated) clusters of flat crystal platelets consisting of epitactically grown HAP nanocrystals and smooth areas between the individual clusters of flat crystal platelets, the % of the surface occupied by the smooth areas between the individual clusters of flat crystal platelets depending on the transformation time in given transformation conditions.

See FIG. 1A, which represents a SEM (Scanning Electron Microscopy) picture of prototype 1 (1-2 mm granules) having a transformation time of 30 min wherein the smooth areas represent about 70% of the total external surface as measured by SEM, and FIG. 1B, which represents a SEM picture of prototype 2 (1-2 mm granule) having a transformation time of 40 min wherein the smooth areas represent about 50% of the total external surface as measured by SEM.

In preparation of the biphasic calcium phosphate/hydroxyapatite (CAP/HAP) bone substitute material disclosed in EP-B1-2445543, it has now been found that by applying a specific washing protocol to the separated granules in step c) of the preparation of the bone graft substitute, the smooth areas of the non-homogeneous external surface between the individual clusters of flat crystal platelets are replaced by coarse areas. The specific washing protocol includes first a defined washing protocol with pure water directly followed by a defined washing protocol with a short-chain aliphatic alcohol. These coarse areas between the individual clusters of flat crystal platelets generally comprise epitactically grown hydroxyapatite platelets forming an interlocked network of platelets with individual platelet sizes of 0.2 to 5 µm as measured by SEM.

It has been further found that when those coarse areas between the individual clusters of flat crystal platelets represent at least 20% of the total external surface as determined by SEM, the osteostimulation (capacity of the bone substitute material to induce new bone formation) is significantly enhanced compared to the bone substitute material disclosed in EP-B1-2445543 transformed under the same conditions but washed with a different washing protocol which results in smooth areas between the individual clusters of flat crystal platelets. This is shown notably by the measurement of bone area density in a femoral condyle defect in a rabbit model after 3 weeks of implantation.

SUMMARY OF THE INVENTION

The invention thus concerns a biphasic calcium phosphate/hydroxyapatite (CAP/HAP) bone substitute material comprising a sintered CAP core and at least one closed epitactically grown layer of nanocrystalline HAP deposited on the external surface of the sintered CAP core, whereby the epitactically grown nanocrystals have the same size and morphology as human bone mineral, wherein the closed epitactically grown layer of nanocrystalline HAP deposited on the external surface of the sintered CAP core has a non-homogeneous external surface comprising individual clusters of flat crystal platelets (consisting of aggregates of epitactically grown HAP nanocrystals) and coarse areas between the individual clusters of flat crystal platelets, whereby the percentage of the coarse areas between the individual clusters of flat crystal platelets is at least 20% of the total external surface as measured by SEM.

That biphasic calcium phosphate/hydroxyapatite (CAP/HAP) bone substitute material shows an increased capacity to induce bone formation.

Generally, the coarse areas between the individual clusters consist of epitactically grown platelets of HAP nanocrystals with individual platelet sizes of 0.2 to 5 µm as determined by SEM.

Preferably the percentage of the coarse areas between the individual crystal clusters is at least 30% of the total surface, more preferably at least 40% of the total external surface as measured by SEM.

Generally, the percentage of HAP as measured by XRD in the above biphasic calcium phosphate/hydroxyapatite (CAP/HAP) bone substitute material is at most 10%. Indeed, it has been found that when that percentage exceeds 10%, the individual clusters of flat crystal platelets of epitactically grown HAP nanocrystals generally occupy too much space in the external surface and hence the percentage of the coarse areas between the individual crystal clusters as measured by SEM is below 20% of the total surface.

Preferably the percentage of HAP as measured by XRD is 1 to 5%, more preferably 1.5 to 3.5%.

The sintered CAP core comprises tricalcium phosphate (TCP), notably α-TCP (α-$Ca_3(PO_4)_2$) or β-TCP (β-$Ca_3(PO_4)_2$), and/or tetracalcium phosphate (TTCP) $Ca_4(PO_4)_2O$.

According to a frequently used embodiment the sintered CAP core essentially consists of TCP, α-TCP being preferred.

The epitactically grown layer of nanocrystalline HAP is structurally nearly identical to the natural human bone mineral.

The CAP/HAP bone substitute material may be a particulate or a granulate, the particles or granules having a desired size and shape. Generally, the particles or granules have a size of 250 to 5000 µm, preferably 1000 to 2000 µm.

The CAP/HAP bone substitute material may also be a shaped body, e.g. a screw, a nail, a pin or a structure having the profile of an osseous body part such as notably a hip, a clavicle, a rib, a mandible or a skull part. Such a screw, a nail or a pin may be used in reconstructive orthopedic surgery for fixing a ligament to a bone, for example in the knee or the elbow. Such a structure having the profile of an osseous body part may be used in orthopedic surgery as prosthesis for replacing a missing or defective bone or bone part.

The invention also relates to a putty comprising particles or granules of the above defined CAP/HAP bone substitute in a suitable matrix, generally comprising natural or synthetic polymers. Generally, the particles or granules have a size of 250 to 5000 µm, preferably 1000 to 2000 µm.

The invention further relates to a process of preparing the above defined CAP/HAP bone substitute material comprising the steps of
a) preparing a sintered CAP core material,
b) immersing the sintered CAP core material in an aqueous buffer solution at a temperature between 10° C. and 50° C. to start the transformation process of CAP to HAP whereby a uniform and closed epitactic grown layer of nanocrystalline hydroxyapatite will be formed on the sintered CAP core material surface, the epitactically grown nanocrystals having the same size and morphology as human bone mineral,
c) stopping the transformation by separating solid material from the aqueous buffered solution at a time when a uniform and closed coating of at least one nanocrystalline layer of HAP is present but before the transformation process is finished completely, washing the separated solid material by applying a specific washing protocol including pure water and a short-chained aliphatic alcohol solution as washing solutions and
d) optionally sterilizing the separated material coming from step c).

The specific washing protocol of step c) of the separated solid material includes between 1 and 10 washing steps, but more preferably between 3 and 7 washing steps, with pure water directly followed by at least one washing step, but more preferably at least two washing steps, with an aliphatic alcohol solution.

A suitable short chain aliphatic alcohol may be selected from the group consisting of methanol, ethanol, propanol and butanol.

Preferably the short chain aliphatic alcohol is ethanol.

The aqueous buffer solution used in step b) is chosen such that the pH value of the immersing solution of step b) is nearly neutral and remains stable throughout the transformation process, preferably within a pH range from 5.5 to 9.0, more preferably from 7.0 to 8.0.

The buffer may be any buffer in the above pH range but is preferably a phosphate buffer with or without calcium, magnesium and/or sodium. A suitable buffer solution is e.g. 0.4 M aqueous solution of sodium dihydrogen phosphate ($NaH_2PO_4$) with a pH value of 7.45±0.1.

The temperature range in step b) is generally between 10° C. and 50° C., preferably between 25 and 45° C., more preferably between 35° C. and 40° C.

Preferably step b) is carried out at a temperature of 35 to 40° C. in a phosphate buffer solution of pH from 7.0 to 8.0.

The preparation of the sintered CAP core material may be performed by methods known in the art comprising first mixing powders of calcium hydrogen phosphate ($CaHPO_4$), calcium carbonate and/or calcium hydroxide, then calcining and sintering the mixture within an appropriate temperature range, thereby giving a bulk sintered CAP core material (see e.g. Mathew M. et al., 1977, Acta. Cryst. B33: 1325; Dickens B. et al., 1974, J. Solid State Chemistry 10, 232; and Durucan C. et al., 2002, J. Mat. Sci., 37:963).

A bulk sintered TCP core material may thus be obtained by mixing powders of calcium hydrogen phosphate ($CaHPO_4$), calcium carbonate and/or calcium hydroxide in stoichiometric ratio, calcining and sintering the mixture at a temperature in the range of 1200-1450° C., preferably about 1400° C.

A bulk sintered TTCP core material may also be obtained by the above described process.

The bulk sintered CAP material prepared by such methods may be porous with a porosity of 2 to 80 vol % and a wide distribution of pores. The porosity parameters will be selected according to the intended application of the CAP/HAP bone substitute material.

The sintered CAP core material used in step b) may be
the bulk sintered CAP core material prepared as described above,
a particulate or granulate of sintered CAP core material obtained from the bulk sintered CAP core material prepared as described above, by using conventional methods such as crushing, grinding and/or milling, and sieving, or
a preform of sintered CAP core material having a desired shape and size, e.g. a screw, a nail, a pin or a structure having the profile of an osseous body part.

Such a preform of any desired shape and size may be obtained from the bulk sintered core material prepared as described above, by using well known prototyping techniques such as CNC milling or 3D printing (see for example Bartolo P. et al., 2008, Bio-Materials and Prototyping Applications in Medicine, Springer Science New York, ISBN 978-0-387-47682-7; Landers R. et al., 2002, Biomaterials 23(23), 4437; Yeong W.-Y. et al., 2004, Trends in Biotechnology, 22 (12), 643; and Seitz H. et al., 2005, Biomed. Mater. Res. 74B (2), 782).

The immersing step b) induces in a first phase a first-order phase transition of the CAP core material and therefore the nucleation of HAP nanocrystal precursors. During the second phase the resulting HAP precursors from the first phase will grow and establish a closed (i.e. completely coating) epitactic nanocrystalline composite layer. The first HAP nanocrystal layer must be uniform and closed and epitactically connected to the sintered CAP core material.

During a third phase the first-order phase transition may proceed within the newly formed bilayer composite to further transform the sintered CAP core material (TCP or TTCP) into nanocrystalline HAP. During this third step of phase transition calcium ions will be released for a controllable time by a slow diffusion controlled process until a part of the sintered CAP core material has been transformed into nanocrystalline HAP. The thickness of the HAP layer and therefore the rate of calcium release can be controlled by variation of the transformation time.

The epitactically grown nanocrystalline HAP layer of appropriate thickness will be prepared in-vitro, the transformation of CAP into HAP being stopped before it is completed.

As soon as the CAP/HAP bone substitute material is set in vivo the transformation process of CAP into HAP will be reactivated by contact with the body fluids and the bone substitute material will function as a living-like system forming new hydroxyapatite similar in size and morphology to human bone mineral. During the in vivo phase transformation process the transported calcium ions will be released into the local environment supporting the local calcium equilibrium which is important and beneficial for bone regeneration processes.

Due to different regeneration times of bone defects in differently loaded regions of the body it is important that the rate of calcium release can be controlled. This can be achieved by variation of the thickness of the epitactically grown layer of hydroxyapatite.

Step c) is therefore a very critical step. The exposure time in the aqueous solution of step b) is based upon the thickness of the HAP layer desired. At least one layer of nanocrystalline HAP in epitaxial orientation is necessary. It is essential that the transformation of CAP into HAP is not finished.

The proper exposure time according to the thickness desired can be calculated by using several thermodynamic differential equations well known to the skilled person in the art of calcium phosphates and cement and concrete chemistry.

See for example: Pommersheim, J. C.; Clifton, J. R. (1979) Cem. Conc. Res.; 9:765; Pommersheim, J. C.; Clifton, J. R. (1982) Cem. Conc. Res.; 12:765; and Schlüssler, K. H. Mcedlov-Petrosjan, O. P.; (1990): Der Baustoff Beton, VEB Verlag Bauwesen, Berlin.

Transferring the solution of the above mentioned differential equations to the CAP/HAP system enables the prediction of the phase transition of CAP into HAP and the thickness of the layer such that the epitactic layer of HAP can be prepared in a stable and reproducible manner.

Separating the solid material from the aqueous solution is usually performed by filtration and drying, using techniques well known in the art.

The optional sterilizing step d) may be performed by techniques well known in the art such as gamma-irradiation or X-ray radiation.

The invention also concerns the use of the above defined CAP/HAP bone substitute material, generally in the form of a particulate or a shaped body as an implant or prosthesis for supporting bone formation, bone regeneration, bone repair and/or bone replacement at a defect site in a human or animal.

The invention also relates to a method of promoting bone formation, bone regeneration and/or bone repair at a defect site in a human or animal by implanting the above defined CAP/HAP bone substitute material, generally in the form of a particulate or a shaped body.

Advantage of the CAP/HAP Bone Substitute Material of the Invention

As shown by the measurement of bone area density in a femoral condyle defect in a rabbit model after three weeks of implantation, the biphasic calcium phosphate/hydroxyapatite (CAP/HAP) bone substitute material of the invention with a non-homogeneous external surface comprising individual (separated) clusters of flat crystal platelets consisting of epitactically grown HAP nanocrystals and coarse areas between the individual clusters of flat crystal platelets shows an increased capacity to induce bone formation compared to the bone substitute material disclosed in EP-B1-2445543 which presents a non-homogeneous external surface comprising individual clusters of flat crystal platelets and smooth areas between the individual clusters of flat crystal platelets.

This is in line with the results published by R. A. Gittens et al. in Biomaterials 2011 May, 32(13): 3395-3403, which show that the introduction of nanoscale structures in combination with micro-submicro-scale roughness improves osteoblast differentiation and local factor production, which in turn indicates the potential for improved implant osseointegration in vivo.

BRIEF DESCRIPTION OF THE DRAWINGS

The invention is described in further detail hereinafter with reference to illustrative examples of preferred embodiments of the invention and the accompanying drawing figures, in which.

DETAILED DESCRIPTION

Figure 1A:
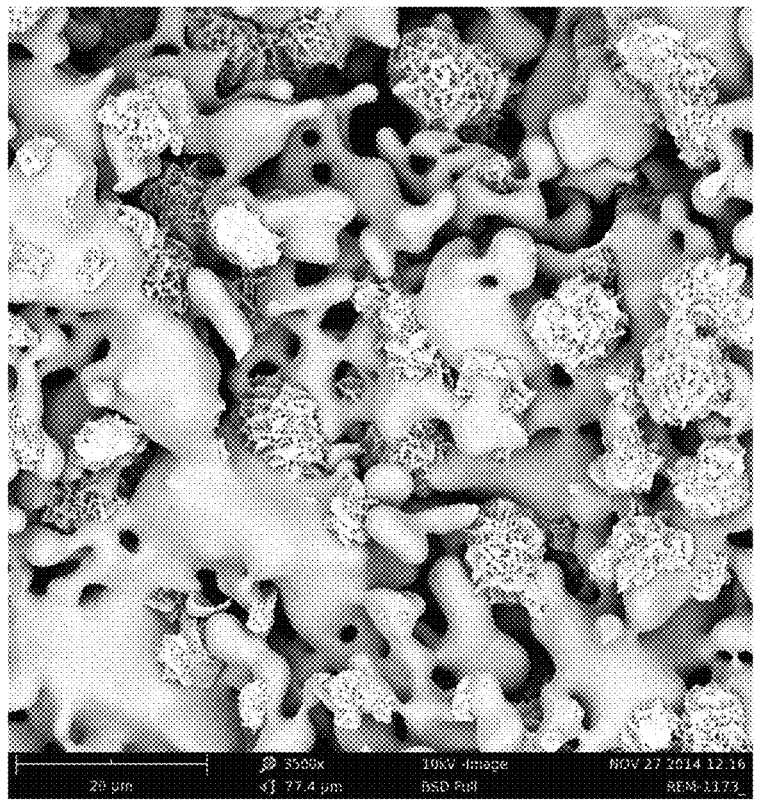
FIG. 1A represents a SEM picture of prototype 1 of a prior art bone substitute prepared in Example 1 according to the disclosure of EP-B1-2445543 with a transformation time of 30 min, wherein the smooth areas between the individual clusters of flat crystal platelets represent about 70% of the total external surface as measured by SEM.

The following examples illustrate the invention without limiting its scope.

Example 1 Preparation of Biphasic Calcium Phosphate/Hydroxyapatite (CAP/HAP) Bone Substitute Materials According to EP-B1-2445543

A bulk sintered material of alpha-TCP, porous granules thereof with a particle size of 1.0-2.0 mm and transformed granules having an epitactically grown HAP coating were prepared similarly to Examples 1, 2 and 4 of EP-B1-2445543.

364 g dicalcium phosphate anhydrous powder, 136 g calcium carbonate powder and 220 ml deionized water were mixed for 5 min at 700 rpm using a laboratory stirrer. The slurry from the mixing process was immediately transferred into a high temperature stable platinum cup. The filled platinum cup was placed in a cold furnace. The furnace was heated to 1400° C. by using a heating rate of 100° C. per hour. This temperature was kept for 12 hours and afterwards the furnace was cooled down to 800° C. with a cooling rate of 500° C. per hour, then cooled down to 300° C. with a cooling rate of 125° C. per hour and finally cooled down to room temperature by switching of the furnace. The bulk sintered material (phase pure α-TCP i.e. α-$Ca_3(PO_4)_2$) was removed from the furnace and the platinum cup. The control of phase purity was performed using powder X-ray diffraction analysis.

The bulk product was crushed by using a jaw crusher (jaw distances varied from 10 to 1 mm). The produced α-TCP granules were sieved by using a sieving machine and sieve inserts with mesh apertures of 2 mm and 1 mm. After sieving, the granules were rinsed with ethanol for separating fine powder residuals adsorbed to the granules. The porous granules were dried for 1 h at 80° C. in a cabinet dryer. The cleanness of the particle surfaces after rinsing was controlled by surface observation using scanning electron microscopy (SEM).

A buffered solution adequate for the coating and phase transformation process was prepared by dissolving 0.4 mol/l sodium dihydrogen phosphate ($NaH_2PO_4$) in distilled water. The pH of the solution was adjusted to 7.45 at room temperature by using sodium hydroxide (NaOH). The granules produced according to the previous paragraphs were immersed into the prepared solution and stored within a well-tempered water bath (40° C.) for 30 min (prototype 1) respectively 40 min (prototype 2). After immersing, the granules were rinsed 3 times with distilled water to stop the phase transformation process and remove residuals from the buffered solution. The porous granules were dried at 100° C. in a cabinet dryer for 2 hours.

Figure 1B:
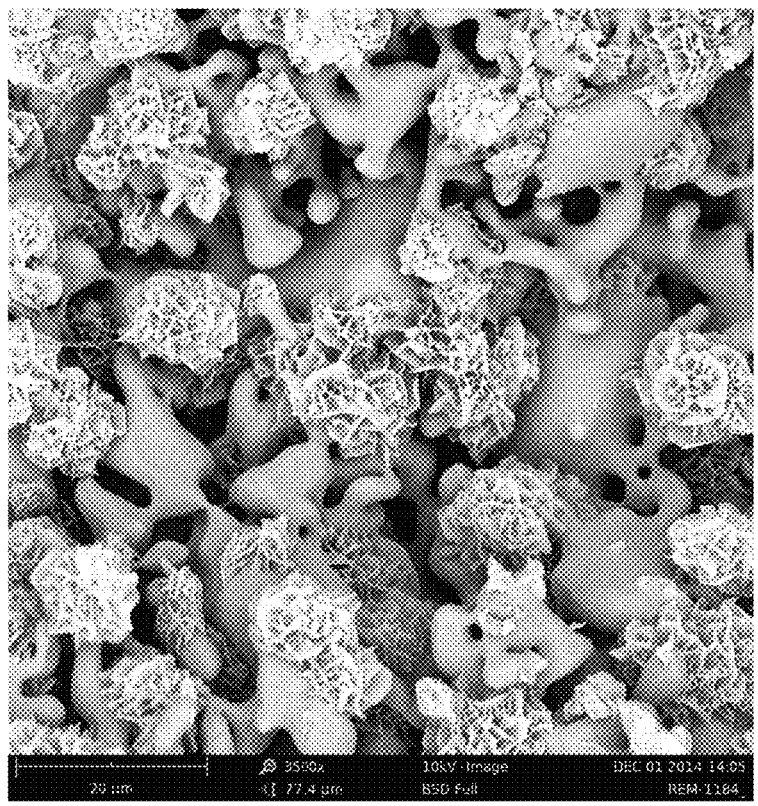
FIG. 1B which represents a SEM picture of prototype 2 of a bone substitute prepared in Example 1 according to the disclosure of EP-B1-2445543 with a transformation time of 40 min, wherein the smooth areas between the individual clusters of flat crystal platelets represent about 50% of the total external surface as measured by SEM.

The surface morphology and surface coverage of crystal clusters after the coating and phase transformation process of prototypes 1 and 2 were observed by scanning electron microscopy (SEM) (see FIG. 1A and FIG. 1B).

As apparent from FIGS. 1A and 1B, the external surface of the granules is non-homogeneous comprising individual clusters of flat crystal platelets consisting of epitactically grown HAP nanocrystals and smooth areas between the clusters.

By measuring the surface occupied by the individual clusters and the smooth areas in between on the SEM pictures for each of prototype 1 and prototype 2, it was determined that the smooth areas represent about 70% of the external surface for prototype 1 and about 50% of the external surface for prototype 2.

Example 2 Preparation of Biphasic Calcium Phosphate/Hydroxyapatite (CAP/HAP) Bone Substitute Materials According to the Invention 1-2 mm sized porous granules of phase pure α-TCP were produced according to above Example 1.

The phase transformation and coating step was performed in glass flasks placed in a water bath set to 40° C. The transformation buffer was a 0.4M aqueous solution of sodium dihydrogen phosphate ($NaH_2PO_4$) with a pH value of 7.45±0.1.

The glass flasks were filled with the transformation buffer and alpha-TCP granules were added with a ratio of 1:40 (granules to transformation solution). The granules were immersed in the transformation solution at 40° C. for 30 min (prototype 3) or 40 min (prototype 4). After immersing, the granules were rinsed 5 times with deionised water (granules to water ratio being 1:10 with respect to weight) and 2 times with Ethanol (99.9%, granules to ethanol ratio being 1:10 with respect to weight) to stop the phase transformation process, induce the formation of the coarse areas and remove residuals from the buffered solution. The porous granules were dried at 100° C. in a cabinet dryer for 2 hours.

Figure 2A:
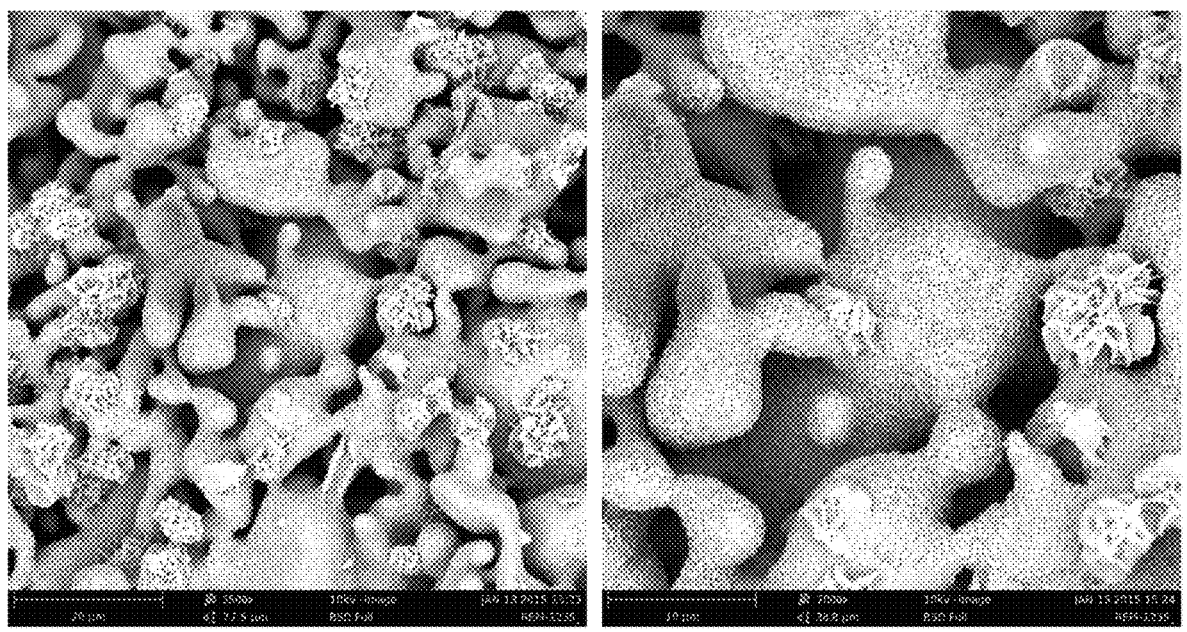
FIG. 2A represents a SEM picture of prototype 3 of a bone substitute material according to the invention prepared in Example 2 with a transformation time of 30 min, wherein the coarse areas between the individual clusters of flat crystal platelets represent about 70% of the total external surface as measured by SEM.
Figure 2B:
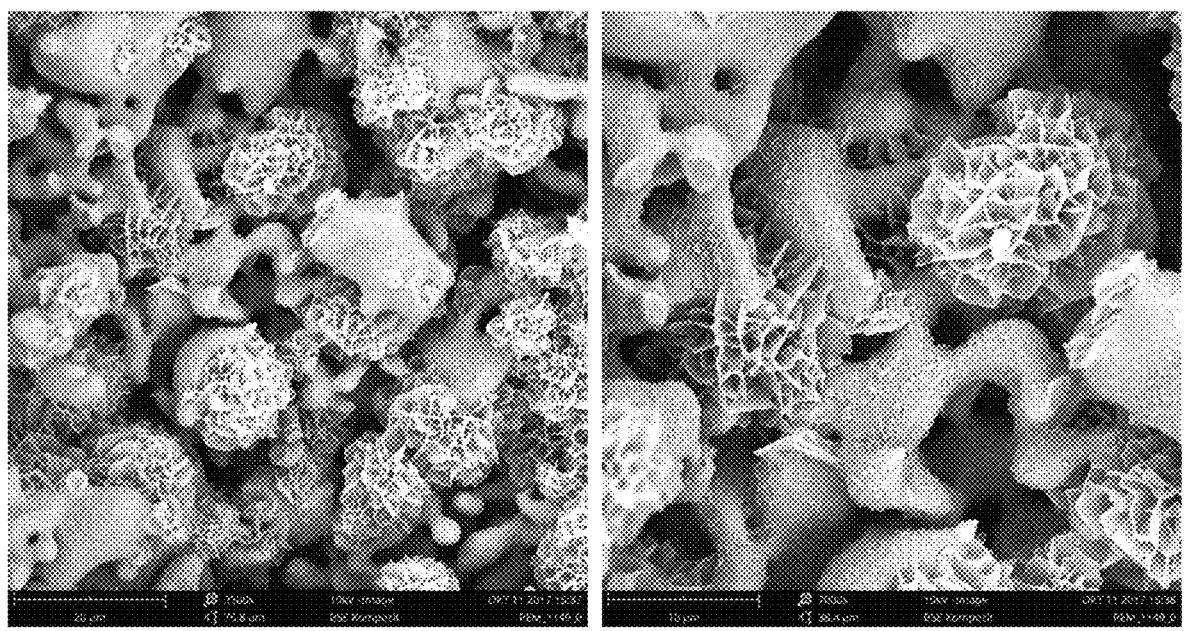
FIG. 2B represents a SEM picture of prototype 4 of a bone substitute material according to the invention prepared in Example 2 with a transformation time of 40 min, wherein the coarse areas between the individual clusters of flat crystal platelets represent about 50% of the total external surface as measured by SEM.

The surface morphology and surface coverage of crystal clusters after the coating and phase transformation process of prototypes 3 and 4 were observed by scanning electron microscopy (SEM) (see FIG. 2A and FIG. 2B).

As apparent from FIGS. 2A and 2B, the external surface of the granules is non-homogeneous comprising individual (separated) clusters of flat crystal platelets consisting of epitactically grown HAP nanocrystals and coarse areas between the clusters.

By measuring the surface occupied by the individual clusters and the coarse areas in-between the clusters on the SEM pictures for each of prototype 3 and prototype 4, it was determined that the coarse areas represent about 70% of the external surface for prototype 3 and about 50% of the external surface for prototype 4.

Example 3 Rabbit Study

To assess the in-vivo performance of the newly developed bone substitute material, a femoral condyle model in the rabbit was chosen. The femoral condyle defect rabbit model is one of the most commonly used animal models to test substitute biomaterials (Li Y. et al. Bone defect animal models for testing efficacy of bone substitute biomaterials, Journal of Orthopaedic Translation (2015) 3, 94-104). Prototypes 1, 2 and 3 as well as competitor materials ACTIFUSE® and NOVABONE® were implanted in New Zealand white rabbits (28 weeks) in a critical sized defect (5 mm×10 mm) in the femoral condyle. After 3 weeks of implantation, the performance of the different biomaterials was analysed by measuring the bone area density, the implant area density, the fibrous area density and the bone marrow area density in the defect for the different prototypes. In order to do a quantitative analysis, the samples were fixed in 10% neutral buffered formalin solution (NBF), embedded in PMMA, cut using the EXACT system and stained with modified Paragon.

Figure 3:
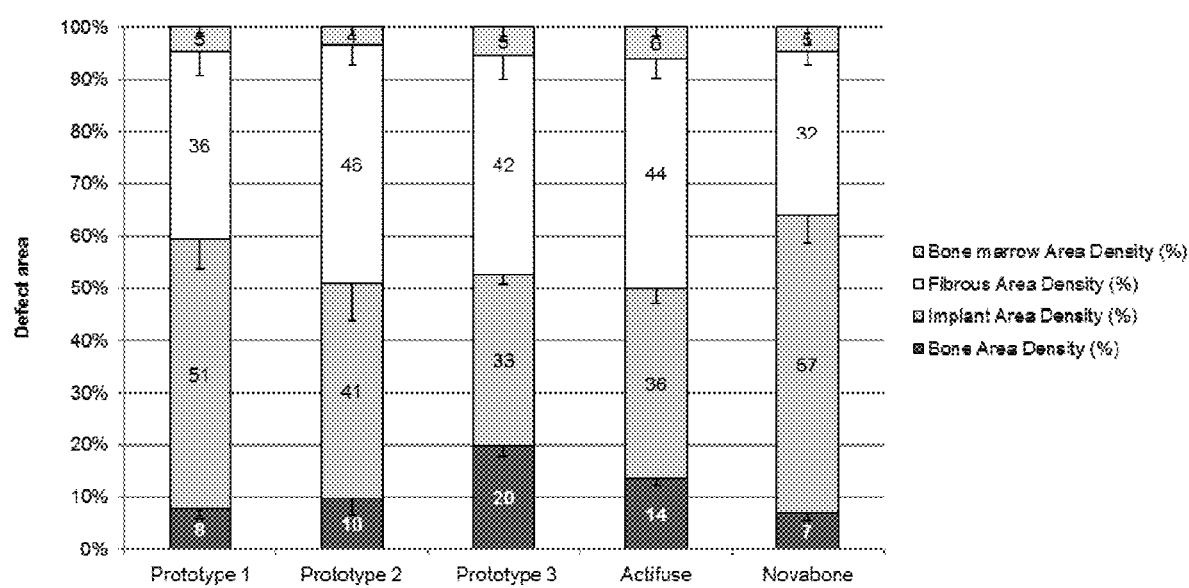
FIG. 3 represents a diagram showing the measurement of bone density in a femoral condyle defect in a rabbit model after three weeks of implantation for the bone substitute material according to the invention of Example 2 (prototype 3), the bone substitute materials according to EP-B1-2445543 of Example 1 (prototypes 1 and 2) and the two well-known commercial bone substitute materials ACTIFUSE® and NOVABONE®.

As shown in FIG. 3, the amount of newly formed bone in a rabbit femoral condyle model was significantly higher for Prototype 3 compared to Prototypes 1 and 2 and competitor materials ACTIFUSE® and NOVABONE® after 3 weeks of implantation.

The invention claimed is:

1. A biphasic calcium phosphate/hydroxyapatite (CAP/HAP) bone substitute material comprising a sintered CAP core and having its total external surface covered by at least one closed epitactically grown layer of nanocrystalline HAP, whereby the epitactically grown nanocrystals have the same size and morphology as human bone mineral, wherein the closed epitactically grown layer of nanocrystalline HAP is transformed from the CAP on the external surface of the sintered CAP core such that the closed epitactically grown layer of nanocrystalline HAP has a non-homogeneous external surface comprising individual clusters of flat crystal platelets consisting of epitactically grown HAP nanocrystals and coarse areas between the individual clusters consisting of platelets of HAP nanocrystals with individual platelet sizes of 0.2 to 5 µm as measured by SEM, whereby the percentage of the coarse areas between the individual clusters as measured by SEM is at least 20% of the total surface of the CAP/HAP bone substitute material.

2. The biphasic calcium phosphate/hydroxyapatite (CAP/HAP) bone substitute material according to claim 1, wherein the percentage of the coarse areas between the individual crystal clusters as measured by SEM is at least 30% of the total surface.

3. The biphasic calcium phosphate/hydroxyapatite (CAP/HAP) bone substitute material according to claim 1, wherein the percentage of the coarse areas between the individual crystal clusters as measured by SEM is at least 40% of the total surface.

4. The biphasic calcium phosphate/hydroxyapatite (CAP/HAP) bone substitute material according to claim 1, wherein the sintered CAP core essentially consists of α-TCP.

5. The biphasic calcium phosphate/hydroxyapatite (CAP/HAP) bone substitute material according to claim 1, wherein the % of HAP as measured by XRD is 1 to 10%.

6. The biphasic calcium phosphate/hydroxyapatite (CAP/HAP) bone substitute material according to claim 1, wherein the % of HAP as measured by XRD is 1.5 to 3.5%.

7. The biphasic calcium phosphate/hydroxyapatite (CAP/HAP) bone substitute material according to claim 1, which is in the form of a granulate.

8. The biphasic calcium phosphate/hydroxyapatite (CAP/HAP) bone substitute material according to claim 1, which is in the form of a shaped body.

9. A putty containing granules of the biphasic calcium phosphate/hydroxyapatite (CAP/HAP) bone substitute material of claim 1 in a polymer matrix.

10. The putty according to claim 9, wherein the granules have a size of 250 to 5000 µm.

11. A process of preparing the CAP/HAP bone substitute material of claim 1, comprising the steps of
a) preparing a sintered CAP core material,
b) immersing the sintered CAP core material in an aqueous buffered solution at a temperature between 10° C. and 50° C. to start a transformation process of CAP to HAP to form a uniform and closed epitactic grown layer of nanocrystalline hydroxyapatite on the sintered CAP core material surface, wherein the epitactically grown nanocrystals have the same size and morphology as human bone mineral,
c) stopping the transformation by separating solid material from the aqueous buffered solution at a time when a uniform and closed coating of at least one nanocrystalline layer of HAP is present but before the transformation process is finished completely, washing the separated solid material by applying a washing protocol including pure water and a short-chained aliphatic alcohol solution as washing solutions to form the CAP/HAP bone substitute material in which the external surface of the sintered CAP core has a non-homogeneous external surface comprising individual clusters of flat crystal platelets consisting of epitactically grown HAP nanocrystals and coarse areas between the individual clusters consisting of platelets of HAP nanocrystals with individual platelet sizes of 0.2 to 5 µm as measured by SEM, wherein the percentage of the coarse areas between the individual clusters as measured by SEM is at least 20% of the total surface of the CAP/HAP bone substitute material, and
d) optionally sterilizing the separated material coming from step c).

12. The process of claim 11, wherein the short-chain aliphatic alcohol is ethanol.

13. The process of claim 11, wherein washing the separated solid material involves 2 to 10 washing steps with pure water directly followed by at least one washing step with a short-chain aliphatic alcohol.

14. The process of claim 11, wherein step b) is carried out at a temperature of 35 to 40° C. in a phosphate buffer solution of pH from 7.0 to 8.0.

15. A method of promoting bone formation, bone regeneration and/or bone repair at a bone defect site in a subject by implanting the CAP/HAP bone substitute material of claim 1, such that bone formation, bone regeneration and/or bone repair are promoted at the bone defect site.

16. The method of claim 15, wherein the CAP/HAP bone substitute material is in the form of a granulate.

17. The method of claim 15, wherein the CAP/HAP bone substitute material is in the form of a shaped body.

18. A method of promoting bone formation, bone regeneration and/or bone repair at a bone defect site in a subject by implanting putty containing granules of a biphasic calcium phosphate/hydroxyapatite (CAP/HAP) bone substitute material according to claim 1 in a polymer matrix.

* * * * *